(12) United States Patent
Nash et al.

(10) Patent No.: US 11,676,514 B2
(45) Date of Patent: *Jun. 13, 2023

(54) SIMULATION SYSTEMS AND METHODS FOR ULTRASOUND GUIDED REGIONAL ANESTHESIA

(71) Applicant: Maverick Regional Anesthesia Education, LLC, Iola, TX (US)

(72) Inventors: Daniel Nash, Edmond, OK (US); David Gaskin, Iola, TX (US)

(73) Assignee: Maverick Regional Anesthesia Education, LLC, Iola, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/669,506

(22) Filed: Feb. 11, 2022

(65) Prior Publication Data
US 2022/0165181 A1 May 26, 2022

Related U.S. Application Data

(63) Continuation of application No. 16/333,327, filed as application No. PCT/US2018/014348 on Jan. 19, 2018, now Pat. No. 11,250,728.

(60) Provisional application No. 62/448,576, filed on Jan. 20, 2017, provisional application No. 62/535,379, filed on Jul. 21, 2017.

(51) Int. Cl.
| G09B 23/28 | (2006.01) |
| G09B 23/30 | (2006.01) |
| A61M 1/00 | (2006.01) |
| A61M 5/168 | (2006.01) |

(52) U.S. Cl.
CPC ......... *G09B 23/286* (2013.01); *G09B 23/285* (2013.01); *G09B 23/303* (2013.01); *A61M 1/774* (2021.05); *A61M 5/16827* (2013.01)

(58) Field of Classification Search
CPC .. G09B 23/286; G09B 23/285; G09B 23/303; A61M 1/774; A61M 5/16827
USPC ............................................................ 434/83
See application file for complete search history.

(56) References Cited

U.S. PATENT DOCUMENTS

| 5,320,537 A | 6/1994 | Watson |
| 5,690,815 A | 11/1997 | Krasnoff et al. |
| 2004/0033477 A1 | 2/2004 | Ramphal et al. |

(Continued)

OTHER PUBLICATIONS

The International Searching Authority, International Search Report and the Written Opinion of the International Searching Authority dated Jun. 27, 2018 in International Application No. PCT/US2018/014348, 11 pages.

(Continued)

*Primary Examiner* — Robert P Bullington
(74) *Attorney, Agent, or Firm* — Trop, Pruner & Hu, P.C.

(57) ABSTRACT

An embodiment includes a system comprising: an artery, a vein, and a nerve; a first length of tubing adjacent at least one of the vein, artery, and nerve; a second length of tubing to couple to the first length of tubing; and a pump comprising a number of actuators; wherein when the system when operating is configured such that (b)(i) the second length of tubing couples to at least one of the number of actuators, (b)(ii) ends of the first and second lengths of tubing are closed, (b)(iii) a second end of the first length of tubing is operatively coupled to a second end of the second length of tubing, (b)(v) the pump pulsates fluid within the first length of tubing in response to the number of actuators intermittently contacting the second length of tubing.

20 Claims, 6 Drawing Sheets

(56) References Cited

U.S. PATENT DOCUMENTS

| | | |
|---|---|---|
| 2004/0124253 A1 | 7/2004 | Bergwin et al. |
| 2006/0027741 A1 | 2/2006 | Faber et al. |
| 2007/0243088 A1 | 10/2007 | North |
| 2009/0053084 A1 | 2/2009 | Klein |
| 2011/0106004 A1 | 5/2011 | Eubanks et al. |
| 2013/0177463 A1 | 7/2013 | Cheng et al. |
| 2013/0288218 A1 | 10/2013 | Mallin et al. |
| 2015/0065988 A1 | 3/2015 | Holderle et al. |
| 2017/0103682 A1 | 4/2017 | Okayama et al. |
| 2017/0268796 A1 | 9/2017 | Takahashi |
| 2018/0177945 A1 | 6/2018 | Sims et al. |
| 2018/0193598 A1 | 7/2018 | Sarkar et al. |

OTHER PUBLICATIONS

Wikipedia, "Peristaltic pump", Jan. 18, 2018, seven pages, https://en.wikipedia.org/wiki/Peristaltic_pump.

Wikipedia, "Pump", Jan. 3, 2018, 14 pages, https://en.wikipedia.org/wiki/Pump.

Liu, et al. "Ultrasound-Guided Regional Anesthesia and Analgesia: A Qualitative Systematic Review", Regional Anesthesia and Pain Medicine, Jan.-Feb. 2009, pp. 47-59, vol. 34, No. 1, American Society of Regional Anesthesia and Pain Medicine.

Morgan, et al. "Development of a Perfused Cadaver Model of Exsanguinating Hemorrhage for Procedural Training and Device Evaluation", The Internet Journal of Medical Simulation, 2014, pp. 1-8, vol. 5, No. 1, Internet Scientific Publications, http://ispub.com/IJMS/5/1/22234.

400

```
┌─────────────────────────────────────────────────────────────────┐
│ Coupling a second length of tubing to a first length of tubing, │
│ wherein (a)(i) the first length of tubing is adjacent a         │
│ neurovascular bundle (NVB), (a)(ii) a first end of the first    │
│ length of tubing is closed and a first end of the second length │
│ of tubing is closed, and (a)(iii) the first length of tubing    │── 401
│ has a first flexibility, the second length of tubing has a      │
│ second flexibility, and the first flexibility is more flexible  │
│ than the second flexibility.                                    │
└─────────────────────────────────────────────────────────────────┘
                                  │
                                  ▼
┌─────────────────────────────────────────────────────────────────┐
│ Collectively filling the first and second lengths of tubing to  │
│ include a volume of fluid that is greater than 80% of the       │
│ collective volume of the first and second lengths of tubing and │── 402
│ less than 100% of the collective volume of the first and second │
│ lengths of tubing.                                              │
└─────────────────────────────────────────────────────────────────┘
                                  │
                                  ▼
┌─────────────────────────────────────────────────────────────────┐
│ Coupling the second length of tubing to a peristaltic pump, the │
│ peristaltic pump comprising a number of rollers that are less   │── 403
│ than four rollers.                                              │
└─────────────────────────────────────────────────────────────────┘
                                  │
                                  ▼
┌─────────────────────────────────────────────────────────────────┐
│ Operating the peristaltic pump to radially pulsate the first    │
│ length of tubing in response to the number of rollers           │── 404
│ intermittently contacting the second length of tubing.          │
└─────────────────────────────────────────────────────────────────┘
```

501 — Locating a first length of tubing adjacent a neurovascular bundle (NVB), wherein (a)(i) a first end of the first length of tubing is closed, and (a)(ii) the first length of tubing has a first flexibility.

502 — Providing a second length of tubing, wherein the (b)(i) the second length of tubing is configured to couple to the first length of tubing, (b)(ii) a first end of the second length of tubing is closed, and (b)(iii) the second length of tubing has a second flexibility that is less flexible than the first flexibility.

503 — Providing a peristaltic pump, wherein (c)(i) the peristaltic pump has a number of predetermined positions for rollers; (c)(ii) the peristaltic pump includes a number of rollers that is less than the number of predetermined positions for rollers.

504 — Containing the first length of tubing and the NVB in a first container.

505 — Containing the peristaltic pump in a second container.

506 — Communicating the first and second containers to a remotely located user.

Fig. 5

SIMULATION SYSTEMS AND METHODS FOR ULTRASOUND GUIDED REGIONAL ANESTHESIA

CROSS-REFERENCE TO RELATED APPLICATIONS

This application is a continuation of U.S. patent application Ser. No. 16/333,327, filed Mar. 14, 2019, which is a § 371 national stage of international application PCT/US2018/014348, filed Jan. 19, 2018, which claims priority to U.S. Provisional Patent Application No. 62/448,576 filed on Jan. 20, 2017 and entitled "Method and Apparatus for High Fidelity Simulation Training of Ultrasound Guided Regional Anesthesia by Making A Cadaveric Specimen Pulsatile" and also claims priority to U.S. Provisional Patent Application No. 62/535,379 filed on Jul. 21, 2017 and entitled "Method and Apparatus for High Fidelity Simulation Training of Ultrasound Guided Regional Anesthesia by Making A Cadaveric Specimen Pulsatile". The content of each of the above applications is hereby incorporated by reference.

TECHNICAL FIELD

Embodiments of the invention relate to high fidelity simulation of medical procedures, particularly for teaching ultrasound guided regional anesthesia (USGRA).

BACKGROUND

As addressed in "Ultrasound-guided regional anesthesia and analgesia: a qualitative systematic review" (Liu S S, Ngeow J E, Yadeau J T. Reg Anesth Pain Med 2009; 34:47-59), the use of ultrasound (US) to guide placement of needles and catheters for regional anesthesia and analgesia (referred to herein as USGRA) has become increasingly popular. The technique is the subject of numerous articles in major anesthesia journals, and many anesthesiology meetings offer lectures and workshops on USGRA. Increased popularity of USGRA may be due to multiple reasons such as "dissatisfaction with success rates of traditional block techniques, preference for a visual endpoint, increased familiarity with ultrasound, overall increased exposure to regional anesthesia, or a belief in increased safety with use of ultrasound guidance." Id.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 4 includes a method in an embodiment.
FIG. 5 includes a method in an embodiment.

DETAILED DESCRIPTION

Figure 1:
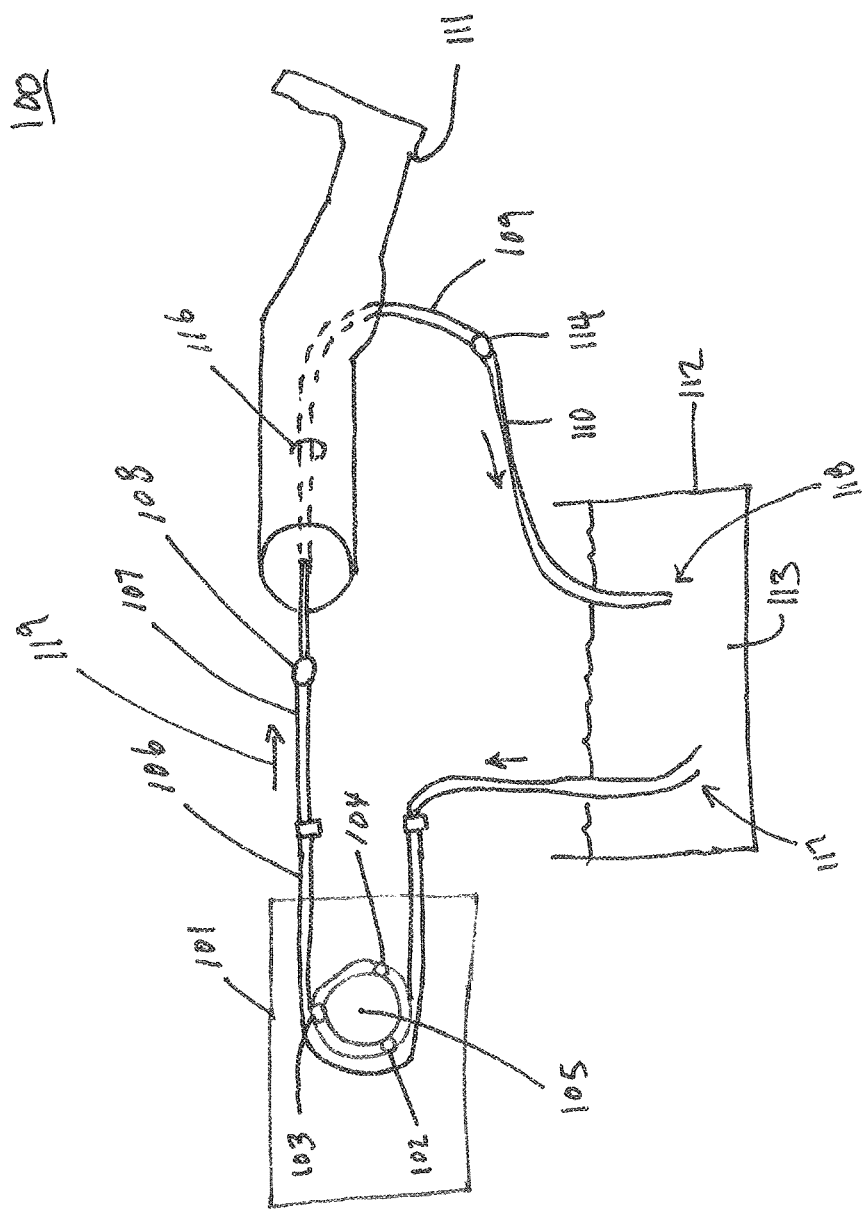
FIG. 1 includes an open end embodiment.

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

As noted above, USGRA is becoming increasingly popular. Consequently, the need to train practitioners with regard to performing USGRA is necessary. However, Applicant determined such training is inadequate. For example, conventional simulation for training in USGRA consists mainly of live human models. Live humans cannot tolerate being repetitively stuck with needles by students learning USGRA. Alternatively, plastic or gel-like models may be used. However, many lack vessels that pulsate so students are unable to palpate such models and ascertain where vessels are, which necessarily complicates locating nerves that are adjacent such vessels. Further, such synthetic models often fail to provide detailed anatomical landmarks. For example, a student may be taught to first locate a certain anatomical feature before then trying to locate a particular nerve. If the model lacks the anatomical feature, then this complicates efforts to teach nerve location based on locating anatomical features. For at least the reasons listed above, training or "practice" of USGRA complicated. In fact, for best results training requires the actual driving of a needle to a target, which is very difficult to accurately simulate with synthetic models.

As a result of the lack of quality training techniques, the primary way for many practitioners to master the skills and required techniques for USGRA is through experience on live subjects. Live patients or animals have been essential in practicing these procedures because the normal pressures of vessels and the touch and feel of a subject's anatomy are crucial elements of practicing successful USGRA. Accordingly, the tendency has been for already experienced providers to be asked to perform whatever procedures are necessary. Thus, there has been a difficulty for inexperienced providers to obtain a desired level of competence. In addition, there is a need to maintain a high degree of skill even for experienced providers that is only possible through continued training. Accordingly, Applicant determined there is a need for providing a life-like experience without obtaining the experience on living persons or animals.

In response to the above, Applicant noted human cadavers have been used for medical training, and provide opportunities for a high fidelity simulation experience in terms of static anatomical landmarks. However, in order to have a truly high fidelity experience, Applicant further determined the trainee needs to be able to feel as though he or she is performing a procedure on an actual live patient.

Embodiments are presented herein that provide high-fidelity models to help train students with regard to USGRA and other procedures. Such models are based on augmentations performed on animal (e.g., human) cadavers. More specifically, an embodiment includes a cadaveric teaching model with simulated pulsatile vasculature. The simulated vasculature may include a flexible tube placed along with or within a neurovascular bundle (NVB). The tube may be attached, directly or indirectly, to a pulsatile pump.

Such models have various benefits. Cadaver-based models necessarily provide a range of variability in human anatomy between different subjects. Also, such models can be utilized to train avoidance of the vasculature (considering the vessels are simply being used as landmarks for the location of nerve bundles and that the student's needle is to avoid the vessels in route to locating a nerve).

However, Applicant determined cadaver models with pulsating vessels provided only part of a solution to effectively teaching USGRA. Applicant experienced various difficulties in rendering a cadaver with pulsating vessels (that mimic arterial pulsation) which could be visualized with US.

For example, Applicant theorized that a "lumen" or "tube" could be passed through arteries of a cadaver and then attached to a pump to mimic flow and pulsation. See, for example, the embodiment of FIG. 1.

FIG. 1 includes system 100 having pump 101. Pump 101 rotates three rollers 102, 103, 104 about axis 105 in a peristaltic manner Conduit 106 couples to conduit 107, valve 108 (e.g., stopcock), conduit 109, valve 114 (e.g., stopcock), and conduit 110. Conduit 109 is included within or alongside a NVB 116 and enters and exits the cadaver portion 111. Opposing ends 117, 118 are open and submerged within the fluid 113 of container 112.

Applicant's first attempts at using pulsatile (e.g., peristaltic) pumps with system 100 were mildly successful and do in fact constitute an embodiment of the invention. Applicant achieved fluid flow 119 within the conduits (e.g., lumens) implanted in cadaver 111 but the flow resulted in weak pulsation of lumen 109 (which a student may palpate in order to find NVB 116). As a result, the US had difficulty visualizing the fluid flow and weak lumen pulsations. Another problem arose when any obstruction to fluid flow occurred. This would cause pump 101 to over pressure the lumen (and/or any tubing coupling the lumen to the pump). This increase in pressure often produced a rupture within the system, which disrupted fluid flow and vessel pulsation.

Nevertheless, system 100 may be utilized to simulate arterial flow for education purposes that require arterial flow (rather than pulsatility). The problem of distal obstruction and lumen rupture or system overload can be remedied by including a check-valve (e.g., in the proximal lumen section of the system) to divert flow in the presence of excess pressure, as shown in FIG. 3.

Figure 3:
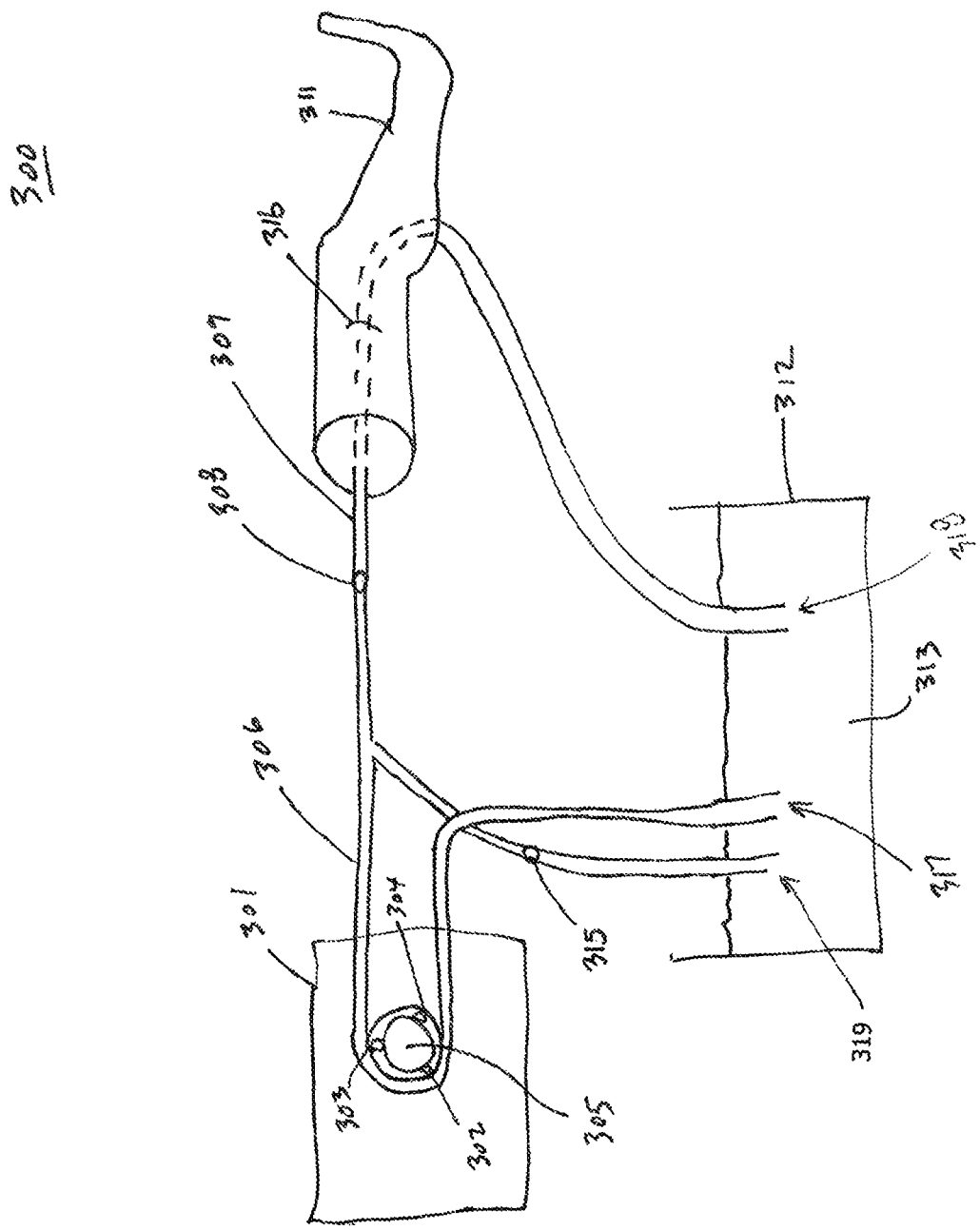
FIG. 3 includes an open end embodiment.

FIG. 3 includes system 300 having pump 301. Pump 301 rotates three rollers 302, 303, 304 about axis 305 in a peristaltic manner Conduit 306 couples to conduit 309, valve 308 (e.g., stopcock), and check valve 315. Conduit 309 is included within or alongside NVB 316 and enters and exits cadaver portion 311. Opposing ends 317, 318 are open and submerged within fluid 313 of container 312. If an obstruction to a conduit (e.g., conduit 309) occurs, pressure will exceed a threshold of check valve 315 and fluid will flow to end 319 to lessen pressure. System 300 is a viable embodiment for teaching.

Nevertheless, Applicant desired an embodiment having increased pulsatility over systems 100, 300. Applicant determined that by having fewer rollers on the pump head, a larger stroke volume would be created in the tubing (which would create a more profound pulse through the lumen, which would be more visible by US). Thus, another embodiment includes system 100, which utilizes only two of rollers 102, 103, 104 (with one of rollers 102, 103, 104 removed). Still another embodiment includes system 300 utilizing only one of rollers 302, 303, 304 (with two of rollers 302, 303, 304 removed). However the two roller system did not allow the fluid-filled tubing system to maintain "prime" (where fluid fills the entire length of tubing between ends 117, 118) and no flow or pulsation (or limited flow or pulsation) would continue once the pump was started. By not keeping the system in constant forward flow the priming pressure was released, thereby stopping all flow (or limiting flow).

Applicant then determined that by closing the fluid filled or "primed" system, the rollers (or roller) would cause a pulse wave to move forward and then the pulse wave would be released until the next roller (or the same roller) caused another forward wave in the closed system. By having a pump roller system that squeezes and releases a fluid wave through the system, a forceful pulsation is created which is more readily seen via US.

Figure 2:
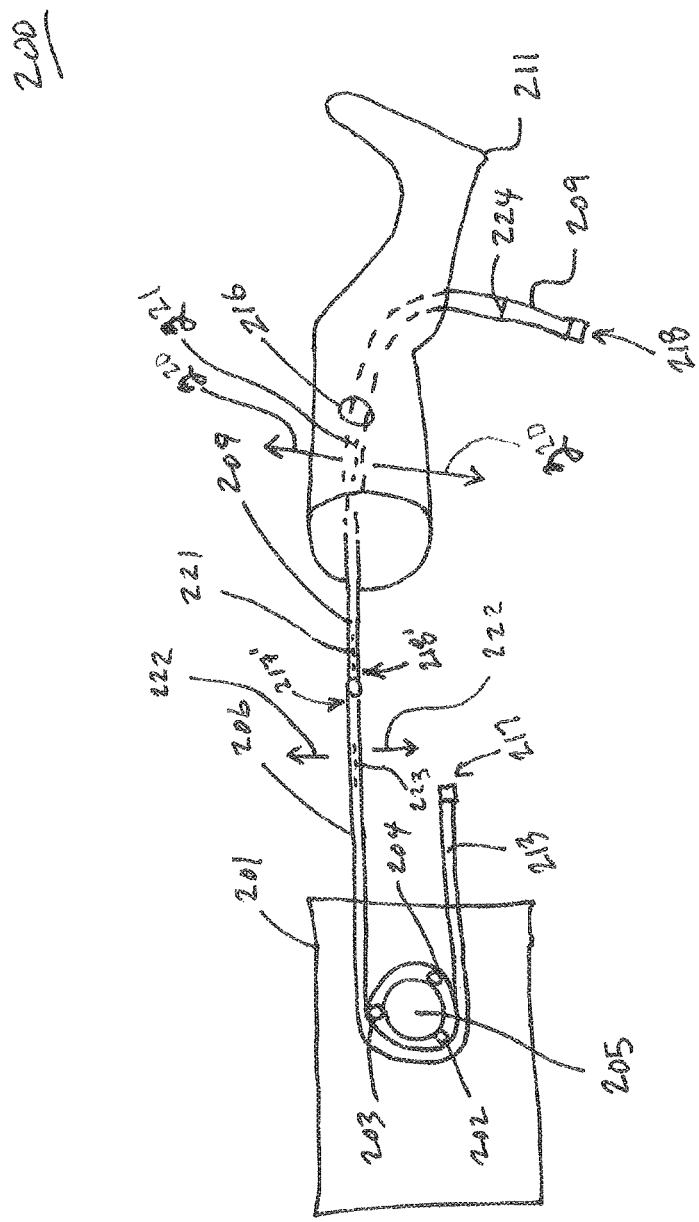
FIG. 2 includes a closed end embodiment.

Thus, an embodiment uses a closed system as seen in FIG. 2. By having a closed, fluid filled system running through an altered peristaltic pump that has only one roller depressing the pump tubing, a series of strong pulses is sent forward in the system allowing easy viewing of a pulse via US. Further, by having a closed system (which can be filled with fluid and then placed in the pump system) the bulky and messy fluid reservoir 112 can be avoided and any obstructions in the system do not cause a buildup of pressure and subsequent rupture of tubing.

FIG. 2 includes system 200 having pump 201. Pump 201 has positons to rotate three rollers 202, 203, 204 about axis 205 in a peristaltic manner (although in embodiments one or two of the rollers are removed to improve pulsatility). Conduit 206 couples to conduit 209. Conduit 209 is included within or alongside NVB 216 and enters and exits cadaver portion 211. Opposing ends 217, 218 are closed. Fluid 213 is included within tubing 206, 209.

System 200 has advantages including: (1) reducing the number of rollers releases the prime in the system, thereby causing conduit 209 to collapse and expand in a pulsatile manner (which is more easily seen with US than weak fluid flow within conduit 209), (2) messy and bulky fluid reservoir 112 is no longer needed, (3) conduit rupture from pressure build up with outflow obstruction is eliminated so the need for check valve 315 and its conduit is negated, and (4) the simplified system 200 allows for faster set up (so teaching can commence more quickly) and faster maintenance in the event of punctured lumen (punctured by a student).

An embodiment includes a system comprising: (1) a pump (such as a peristaltic pump with a single roller), and (2) a length of tubing closed on each of its ends. An embodiment includes a method of use for teaching US-guided nerve blocks.

Also, an embodiment includes a method of preparing a cadaver. The method is based off the following instructions.

(1) Obtain a lightly embalmed cadaver specimen. Fresh cadavers are adequate only for short periods of time due to rapid deterioration of the flesh. Fully embalmed specimens are not pliable and the tissue does not view as well under US. Make arrangements with the embalmer to leave the neck and femoral areas intact. Ask embalmer to not cannulate through the carotid arteries, internal jugular veins, or femoral vessels.

(2) Section the cadaver into upper and lower parts at the low thoracic lumbar region T12-L1. Remove all viscera and chest organs. Disarticulate the arms at the glenohumeral joint, leaving enough flesh along the axilla of the arm and shoulder to simulate the axillary block with high fidelity quality. This makes the passing of the lumens easier as it is a straight line through the axillary to brachial artery NVB. It can be very difficult to reliably pass lumens through intact cadavers. Then excise legs in guillotine fashion straight down along the proximal third of the thigh.

(3) Pass lumens through the femoral NVB (sometimes referred to herein as a neurovascular path). Next pass lumens along the axillary artery subclavian artery NVP. Then pass lumens along the femoral artery NVP. In an embodiment the lumens are ¼ inch in diameter, which will fit through most vasculature or NVBs. Since veins and arteries typically run side by side it is sometimes easier to pass the lumen through the vein as it may be of larger diameter than the artery and have less plaque inhibiting passage of the lumen. If the vein and artery are not able to be used then the lumen can be passed alongside the vessels through the NVB (e.g., NVB sheath) that is typically present. A variety of techniques may be used to pass the lumens. Long (e.g., 18 inches) straight forceps can be pushed though the bundle sheath and then the lumen can be pulled back through while being held by the forceps. A thin, stiff ball-tipped orthopedic guide rod can be passed through the vasculature or bundle. Then a lumen may be tied tightly over the ball tip. The ball tip can then be pulled back through the vessel or bundle sheath (taking with it the lumen). Then the lumen is observed via US to ensure it represents the anatomy accurately. If not, then the lumen needs to be repositioned.

An embodiment includes a process comprising setting up the pump system to render the cadaver parts pulsatile. The method is based on the following instructions.

(1) Obtain a peristaltic pump. Remove all but one roller (so a closed system does not build up pressure, instead only propagating a pulsatile wave with each revolution of the pump head).

(2) Build a tubing system consisting of a span of silastic or soft rubber "pump" tubing of proper size (diameter and length, such as approximately 8 inches of ¼ inch diameter tubing) to fit into pump roller assembly. Close off one end of this span of tubing with a ¼ inch female adapter tightened onto the tubing with a zip tie to keep it from popping off of system when running (e.g., all tubing attachments are attached with zip ties). Attach a 3-way stopcock to this end for filling the lumen system with water. Attach a male ¼ inch adapter to other end of the "pump" tubing. Create a span of ¼ inch polyvinylchloride (PVC) or plastic tubing of sufficient length to reach from the pump (i.e., pump tubing) to the cadaver piece and lumen (e.g., approximately 3 feet). One end of this tubing has a male adapter and one end has a female adapter zip tied in place. Use female adapters on all tubing coming FROM the cadaver and all male ends on tubing going TO the cadaver to avoid mismatched attachments. Assemble the pump tubing and the other tubing section together. Attach the male adapter of the tubing to a female adapter zip tied to one end of the cadaver lumen via a 3 way stopcock assembly. This will allow you to fill the length of tubing up to the cadaver lumen stopcock with water and close off this filled system. Leave the other end of the cadaver lumen open to allow the lumen to be filled with water.

(3) Using a large 60 cc syringe on the distal end of the pump tubing, fill the entire system with water and tie off the distal end of the cadaver lumen leaving a fully closed water filled tubing system. Attempt to remove all bubbles and air.

(4) Place the "pump" tubing into the 1 roller pump assembly of the pump. Be sure the roller will rotate in the direction of the cadaver to promote the pulse wave through the lumen. The closed, water filled system (when turned on and functioning) will now create a pulsatile wave through the cadaver lumen that can easily be seen on the screen of a US machine.

An embodiment includes utilization of the lumen and pulsatile pump system to teach a nerve block. With the pump system running and attached to a lumen within a cadaver specimen, the student can visualize the pulse of the lumen with US. The pulsatile image will give the student a realistic view of the normal human anatomy. This allows the student to identify the nerve structures as they relate to the vessels in normal human subjects. They can then repetitively perform the various nerve blocks being taught.

In an embodiment the model includes flexible tubings, such as silicone or polyvinyl tubing, and other types of pulsatile fluid pumps, including diaphragm and piston/syringe pumps.

Again regarding FIG. 2, an embodiment includes a system 200 comprising: NVB 216 comprising an artery, a vein, and a nerve. The artery directly contacts at least one of the vein and the nerve. The vein directly contacts at least one of the artery and the nerve. The nerve directly contacts at least one of the vein and the artery. In a typical NVB of a cadaver segment, the artery, vein, and nerve would be closely coupled to each other within a sheath or confluence of muscles. While a leg is shown in FIG. 2, the NVB may be in various locations and include, for example, an axillary NVB, a femoral NVB, a popliteal NVB, and a brachial NVB.

System 200 includes a first length of tubing 209 directly contacting at least one of the vein, the artery, and the nerve of NVB 216. To obtain the best results for the student, lumen 209 (which will pulsate as if it were the artery of NVB 216 once pump 201 begins pumping) is more realistic the closer lumen 209 is to the vessels of NVB 216. The tubing may be within NVB 216 (e.g., within a sheath of NVB 216) or within a vessel of NVB 216 (e.g., within one of one or more arteries in NVB 216 or within one of one or more veins of NVB 216).

System 200 includes a second length of tubing 206 coupled to the first length of tubing 209. Peristaltic pump 201 comprises a number of rollers and in an embodiment the number of rollers is no more than three rollers. For example, FIG. 2 shows three locations for rollers. In FIG. 2 those locations are filled by rollers 202, 203, 204. However, in other embodiments one of those rollers may be removed (thereby leaving a roller location unoccupied by a roller) to help promote a loss of prime during pumping (which will facilitate more drastic radial pulsation along lines 220, which are orthogonal to long axis 221). In other embodiments two of those rollers may be removed (thereby leaving two roller locations unoccupied by a roller) to help promote a loss of prime during pumping (which will facilitate more drastic radial pulsation along lines 220, which are orthogonal to long axis 221).

System 200 may include various orientations or configurations. One such orientation is addressed herein as an "operative orientation". System 200 may be shipped to customers in various boxes and the like. During that time, the system is not in an "operative orientation". For example, a cadaver portion with a NVB may already include tubing 209 within the NVB. That cadaver (and tubing 209) may be shipped to a user while enclosed in a first container (e.g., a box). Tubing 206 and pump 201 may be shipped to the user in a second container (e.g., a box).

The user may then achieve the "operative orientation" by coupling tubing 206 to 209, turning the pump 201 on, and allowing the rollers (depending on how many rollers were included in the box considering there may be one or more "blank" spots that could have a roller but in fact have no roller) to rotate at a certain rate (measured in revolutions per minute about axis 205). In the "operative orientation" the second length of tubing 206 directly contacts at least one of the rollers. In FIG. 2 rollers 202 and 203 are providing such contact. The first end 218 of the first length of tubing 209 is closed and second end 218' of the first length of tubing is open. A first end 217 of the second length of tubing 206 is closed and a second end 217' of the second length of tubing is open. The second end 218' of the first length of tubing is communicatively coupled (e.g., via male and female adapters on ends 217', 218') to the second end 217' of the second length of tubing. Thus, this is a "closed system" where no complete circuit is formed. In other words, the fluid does not (as would be the case with an "open system") begin its travel at roller 203, advance through tubing 206, 209, enter into a pool (see container 112), and then return to roller 203.

In the "operative orientation" the peristaltic pump 201 reciprocally moves fluid back and forth within the first and second lengths of tubing 209, 206 in response to the roller(s) intermittently contacting the second length of tubing 206. Considering ends 217, 218 are closed (via tie wrap, suture, closed valve, tube tied in a knot, and the like) the fluid advances and recedes based on the state of any roller in contact with tube 206. For example, if only one of rollers 202, 203, 204 is used then when that one roller is in contact with tube 206 and advancing/revolving in a forward/clockwise manner about axis 205, then the fluid is moving towards end 218. After the single roller disengages tube 206 the fluid will move back towards end 217. In so doing there will be palpable pulsation along lines 220 (tube 209 will bulge and collapse based on the pulsations).

As used herein, a peristaltic pump is a type of positive displacement pump used for pumping a variety of fluids. The fluid is contained within a flexible tube fitted inside a circular pump casing (though linear peristaltic pumps also exist and are included in various embodiments described herein). A rotor with a number of "rollers", "shoes", "wipers", or "lobes" attached to the external circumference of the rotor compresses the flexible tube. As the rotor turns, the part of the tube under compression is pinched closed (or "occludes") thus forcing the fluid to be pumped to move through the tube. Additionally, as the tube opens to its natural state after the passing of the cam ("restitution" or "resilience") fluid flow is induced to the pump. This process is called peristalsis and is used in many biological systems such as the gastrointestinal tract.

In various embodiments only 1 roller is in contact with tube 206 at any given time (regardless of whether the system has more than one roller attached to the hub that circulates about axis 205). In various embodiments only 2 rollers are simultaneously in contact with tube 206 at any given time. In various embodiments 3 or more rollers are simultaneously in contact with tube 206 at any given time.

In system 200 the first length of tubing 209 has a first flexibility; the second length of tubing 206 has a second flexibility; and the first flexibility is more flexible than the second flexibility. As a result, the energy or pressure created by advancement of a roller is directed more to the tubing adjacent NVB 216 (where a student may be palpating and/or using US to locate a pulsating vessel, then indirectly locate a nerve that should be blocked) and less towards tubing 206. If the majority of the pressure/energy were expended pulsating tube 206 then the level of pulsation of tube 209 along line 220 may be diminished.

As mentioned above, the first length of tubing 209 includes a first long axis 221. As used herein, this long axis is to be visualized when the first length of tubing is straight (i.e., see the portion of tubing 209 immediately adjacent end 218'), from the first end of the first length of tubing to the second end of the first length of tubing. The second length of tubing 206 includes a second long axis 223 that extends, when the second length of tubing is straight, from the first end of the second length of tubing to the second end of the second length of tubing. The first flexibility is configured so the tubing will pulsate in a direction 220 orthogonal to the first long axis 221 in response to the peristaltic pump reciprocally moving fluid back and forth within the first and second lengths of tubing at a rate. In an embodiment the second flexibility is configured so the second tubing does not pulsate in a direction 222 orthogonal to the second long axis 223 in response to the peristaltic pump reciprocally moving fluid back and forth within the first and second lengths of tubing at a rate.

In an embodiment the first and second lengths of tubing 209, 206 collectively include a volume of fluid 213. A first portion of the volume of fluid is included in the first length of tubing 209 and a second portion of the volume of fluid is included in the second length of tubing 206. The peristaltic pump 201, the first length of tubing 209, the second length of tubing 206, and the volume of fluid 213 are configured to lose prime when the peristaltic pump pumps at a rate of revolutions per minute. For example, depending on the number of rollers in use the pump may generate more than one pulse along lines 220 for every one complete rotation of a roller about axis 205.

Generally regarding pumps, the feed line of a pump and the internal body surrounding the pumping mechanism are typically first filled with the liquid that requires pumping. In other words, an operator must introduce liquid into the system to initiate the pumping. This is called priming the pump. Loss of prime is usually due to ingestion of air into the pump. As used herein, a "loss of prime" means there is air within a section of tubing lengths 206, 209 at some point in time (e.g., when a single roller has compressed the tubing but is no longer compressing the tubing). Certainly some embodiments may function with no air within the lengths 206, 209 and they may still generate pulses along lines 220. However, the magnitude of those movements along lines 220 can be more dramatic in some conditions when there is "loss of prime" (air in a section of tubes 206 and/or 209) because such a loss may coincide with a very flexible tube actually collapsing and then bulging in repeatable fashion.

In an embodiment at least one of the first and second lengths of tubing includes a visual marker 224 that indicates when the first and second lengths of tubing collectively include the volume of fluid that will result in a the desired amount of pulsatility along lines 220. The visual marker is not located at the first end 218 of the first length of tubing or at the first end 217 of the second length of tubing.

In an embodiment the first and second lengths of tubing collectively comprise a collective volume configured to retain the fluid (i.e., the volume between ends 217, 218 regardless of whether fluid is in the tubing). The volume of fluid between end 217 and marker 224 is greater than 80% of the collective volume (i.e., the volume between ends 217, 218) and less than 100% of the collective volume (i.e., the volume between ends 217, 218).

FIG. 4 includes a method 400.

Block 401 includes coupling a second length of tubing to a first length of tubing, wherein (a)(i) the first length of tubing is adjacent a neurovascular bundle (NVB), (a)(ii) a first end of the first length of tubing is closed and a first end of the second length of tubing is closed, and (a)(iii) the first length of tubing has a first flexibility, the second length of tubing has a second flexibility, and the first flexibility is more flexible than the second flexibility. Closure of the first ends of the first and second lengths of tubing may occur later or earlier in the process in other embodiments. In some embodiments the coupling of the lengths of tubing may have already been performed before the process begins.

Block 402 includes collectively filling the first and second lengths of tubing to include a volume of fluid that is greater than 80% of the collective volume of the first and second lengths of tubing and less than 100% of the collective volume of the first and second lengths of tubing. In other embodiments, the filling stage may occur before the process 400 begins.

Block 403 includes coupling the second length of tubing to a peristaltic pump, the peristaltic pump comprising a number of rollers that are less than four rollers.

Block 403 includes operating the peristaltic pump to radially pulsate the first length of tubing in response to the number of rollers intermittently contacting the second length of tubing.

FIG. 5 includes a method 500.

Block 501 includes locating a first length of tubing adjacent a neurovascular bundle (NVB), wherein (a)(i) a first end of the first length of tubing is closed, and (a)(ii) the first length of tubing has a first flexibility. In an embodiment the tube can be closed at a later time.

Block 502 includes providing a second length of tubing, wherein the (b)(i) the second length of tubing is configured to couple to the first length of tubing, (b)(ii) a first end of the second length of tubing is closed, and (b)(iii) the second length of tubing has a second flexibility that is less flexible than the first flexibility. In an embodiment the tube can be closed at a later time.

Block 503 includes providing a peristaltic pump, wherein (c)(i) the peristaltic pump has a number of predetermined positions for rollers; and (c)(ii) the peristaltic pump includes a number of rollers that is less than the number of predetermined positions for rollers.

Block 504 includes containing the first length of tubing and the NVB in a first container.

Block 505 includes containing the peristaltic pump in a second container.

Block 506 includes communicating the first and second containers to a remotely located user. Such a user may include, for example, a hospital or a group at a scientific congress or meeting. Communication may include shipping boxes.

In an embodiment method 500 includes (wherein the first and second lengths of tubing collectively comprise a collective volume configured to retain the fluid) (a) communicatively coupling the first and second lengths of tubing to each other; and (b) collectively filling the first and second lengths of tubing to include a volume of fluid that is greater than 80% of the collective volume and less than 100% of the collective volume. This would occur before block 506.

Figure 6:
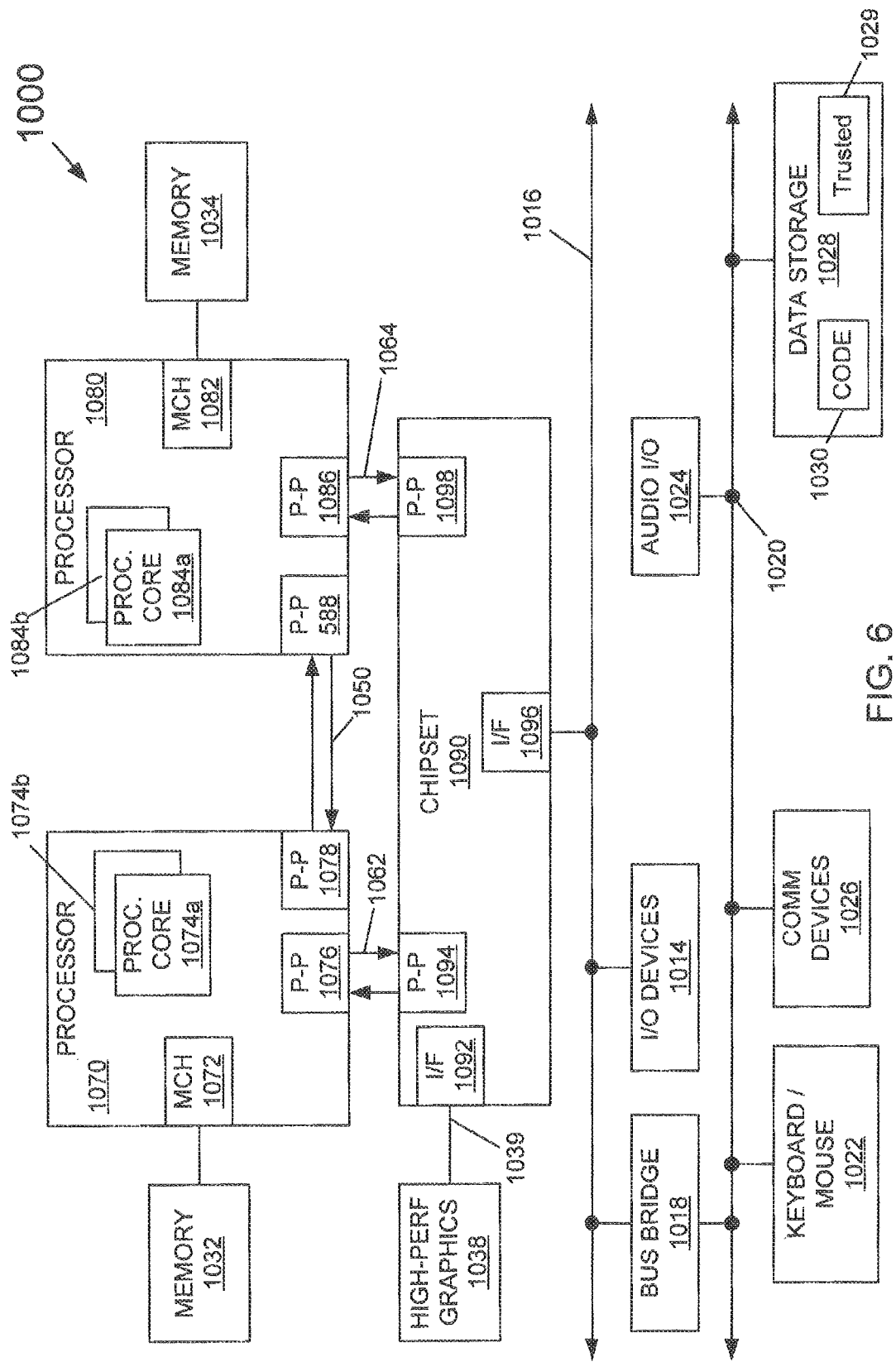
FIG. 6 includes a system for use with an embodiment.

Pump 201 may include (or couple to) a computer to drive pumping. Such a computer may include the system of FIG. 6. In FIG. 6 multiprocessor system 1000 is a point-to-point interconnect system such as a server system, and includes a first processor 1070 and a second processor 1080 coupled via a point-to-point interconnect 1050. Each of processors 1070 and 1080 may be multicore processors such as SoCs, including first and second processor cores (i.e., processor cores 1074a and 1074b and processor cores 1084a and 1084b), although potentially many more cores may be present in the processors. In addition, processors 1070 and 1080 each may include a secure engine 1075 and 1085 to perform security operations such as attestations, IoT network onboarding or so forth.

First processor 1070 further includes a memory controller hub (MCH) 1072 and point-to-point (P-P) interfaces 1076 and 1078. Similarly, second processor 1080 includes a MCH 1082 and P-P interfaces 1086 and 1088. MCH's 1072 and 1082 couple the processors to respective memories, namely a memory 1032 and a memory 1034, which may be portions of main memory (e.g., a DRAM) locally attached to the respective processors. First processor 1070 and second processor 1080 may be coupled to a chipset 1090 via P-P interconnects 1052 and 1054, respectively. Chipset 1090 includes P-P interfaces 1094 and 1098.

Furthermore, chipset 1090 includes an interface 1092 to couple chipset 1090 with a high performance graphics engine 1038, by a P-P interconnect 1039. In turn, chipset 1090 may be coupled to a first bus 1016 via an interface 1096. Various input/output (I/O) devices 1014 may be coupled to first bus 1016, along with a bus bridge 1018 which couples first bus 1016 to a second bus 1020. Various devices may be coupled to second bus 1020 including, for example, a keyboard/mouse 1022, communication devices 1026 and a data storage unit 1028 such as a non-volatile storage or other mass storage device. As seen, data storage unit 1028 may include code 1030, in one embodiment. As further seen, data storage unit 1028 also includes a trusted storage 1029 to store sensitive information to be protected. Further, an audio I/O 1024 may be coupled to second bus 1020.

Program instructions may be used to cause a general-purpose or special-purpose processing system that is programmed with the instructions to perform the operations described herein. Such instructions may include pump rates and the like for pump 201. Alternatively, the operations may be performed by specific hardware components that contain hardwired logic for performing the operations, or by any combination of programmed computer components and custom hardware components. The methods described herein may be provided as (a) a computer program product that may include one or more machine readable media having stored thereon instructions that may be used to program a processing system or other electronic device to perform the methods or (b) at least one storage medium having instructions stored thereon for causing a system to perform the methods. The term "machine readable medium" or "storage medium" used herein shall include any medium that is capable of storing or encoding a sequence of instructions (transitory media, including signals, or non-transitory media) for execution by the machine and that cause the machine to perform any one of the methods described herein. The term "machine readable medium" or "storage medium" shall accordingly include, but not be limited to, memories such as solid-state memories, optical and magnetic disks, read-only memory (ROM), programmable ROM (PROM), erasable PROM (EPROM), electrically EPROM (EEPROM), a disk drive, a floppy disk, a compact disk ROM (CD-ROM), a digital versatile disk (DVD), flash memory, a magneto-optical disk, as well as more exotic mediums such as machine-accessible biological state preserving or signal preserving storage. A medium may include any mechanism for storing, transmitting, or receiving information in a form readable by a machine, and the medium may include a medium through which the program code may pass, such as antennas, optical fibers, communications interfaces, and the like. Program code may be transmitted in the form of packets, serial data, parallel data, and the like, and may be used in a compressed or encrypted format. Furthermore, it is common in the art to speak of software, in one form or another (e.g., program, procedure, process, application, module, logic, and so on) as taking an action or causing a result. Such expressions are merely a shorthand way of stating that the execution of the software by a processing system causes the processor to perform an action or produce a result.

A module as used herein refers to any hardware, software, firmware, or a combination thereof. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices. However, in another embodiment, logic also includes software or code integrated with hardware, such as firmware or micro-code.

Various examples are now addressed.

Example 1 includes a system comprising: a neurovascular bundle (NVB) comprising an artery, a vein, and a nerve, wherein (a)(i) the artery directly contacts at least one of the vein and the nerve, (a)(ii) the vein directly contacts at least one of the artery and the nerve, and (a)(iii) the nerve directly contacts at least one of the vein and the artery; a first length of tubing directly contacting at least one of the vein, the artery, and the nerve; a second length of tubing coupled to the first length of tubing; and a peristaltic pump comprising a number of rollers and the number of rollers is no more than three rollers; wherein in an operative orientation (b)(i) the second length of tubing is to directly contact at least one of the number of rollers, (b)(ii) a first end of the first length of tubing is closed and a second end of the first length of tubing is open, (b)(iii) a first end of the second length of tubing is closed and a second end of the second length of tubing is open, (b)(iv) the second end of the first length of tubing is communicatively coupled to the second end of the second length of tubing, (b)(v) the peristaltic pump is to reciprocally move fluid back and forth within the first and second lengths of tubing in response to the number of rollers intermittently contacting the second length of tubing.

In another version of Example 1 a system comprises: a neurovascular bundle (NVB) comprising an artery, a vein, and a nerve, wherein (a)(i) the artery directly contacts at least one of the vein and the nerve, (a)(ii) the vein directly contacts at least one of the artery and the nerve, and (a)(iii) the nerve directly contacts at least one of the vein and the artery; a first length of tubing directly contacting at least one of the vein, the artery, and the nerve; a second length of tubing to couple to the first length of tubing; and a peristaltic pump comprising a number of rollers and the number of rollers is no more than three rollers; wherein in an operative orientation (b)(i) the second length of tubing directly contacts at least one of the number of rollers, (b)(ii) a first end of the first length of tubing is closed and a second end of the first length of tubing is open, (b)(iii) a first end of the second length of tubing is closed and a second end of the second length of tubing is open, (b)(iv) the second end of the first length of tubing is communicatively coupled to the second end of the second length of tubing, (b)(v) the peristaltic pump reciprocally moves fluid back and forth within the first and second lengths of tubing in response to the number of rollers intermittently contacting the second length of tubing.

The system of example 1 may be included in various boxes. For example, the system may have the NVB in a first box and the pump in a second box. The boxes may be shipped separately to a customer, yet still constitute the system.

Example 2 includes the system of claim 1 wherein the number of rollers is no more than two rollers.

Example 3 includes the system of claim 2 wherein the first length of tubing is included in one of the artery and the vein.

Example 4 includes the system of claim 2 wherein: the first length of tubing has a first flexibility; the second length of tubing has a second flexibility; the first flexibility is more flexible than the second flexibility.

Example 5 includes the system of claim 4 wherein: the first length of tubing includes a first long axis that extends, when the first length of tubing is straight, from the first end of the first length of tubing to the second end of the first length of tubing; the second length of tubing includes a second long axis that extends, when the second length of tubing is straight, from the first end of the second length of tubing to the second end of the second length of tubing; the first flexibility is configured to pulsate in a direction orthogonal to the first long axis in response to the peristaltic pump reciprocally moving fluid back and forth within the first and second lengths of tubing at a rate;

Example 6 includes the system of claim 5 wherein the second flexibility is configured to not pulsate in a direction orthogonal to the second long axis in response to the peristaltic pump reciprocally moving fluid back and forth within the first and second lengths of tubing at a rate.

Example 7 includes the system of claim 5 wherein the NVB is selected from the group consisting of an axillary NVB, a femoral NVB, a popliteal NVB, and a brachial NVB.

Example 8 includes the system of claim 4 wherein: the first and second lengths of tubing collectively include a volume of fluid; a first portion of the volume of fluid is included in the first length of tubing; a second portion of the volume of fluid is included in the second length of tubing; the peristaltic pump, the first length of tubing, the second length of tubing, and the volume of fluid are configured to lose prime when the peristaltic pump pumps at a rate of revolutions per minute.

Example 9 includes the system of claim 8 wherein: the at least one of the first and second lengths of tubing includes a visual marker that indicates when the first and second lengths of tubing collectively include the volume of fluid; the visual marker is not located at the first end of the first length of tubing; the visual marker is not located at the first end of the second length of tubing; the visual marker is located between the first end of the first length of tubing and the first end of the second length of tubing.

Example 10 includes the system of claim 8 wherein: the first and second lengths of tubing collectively comprise a collective volume configured to retain the fluid; the volume of fluid is greater than 80% of the collective volume and less than 100% of the collective volume.

Example 11 includes the system of claim 4 wherein: at least one of the first and second lengths of tubing includes a visual marker that indicates when the first and second lengths of tubing collectively include a volume of fluid; the first and second lengths of tubing collectively comprise a collective volume configured to retain the volume of fluid; the volume of fluid is greater than 80% of the collective volume and less than 100% of the collective volume; a first portion of the volume of fluid is to be included in the first length of tubing; a second portion of the volume of fluid is to be included in the second length of tubing; the peristaltic pump, the first length of tubing, the second length of tubing, and the volume of fluid are configured to lose prime when the peristaltic pump pumps at a rate of revolutions per minute.

Example 12 includes the system of claim 11 wherein: the first length of tubing includes a long axis that extends, when the first length of tubing is straight, from the first end of the first length of tubing to the second end of the first length of tubing; the first length of tubing is configured to collapse and expand, in the direction orthogonal to the long axis, in response to both (c)(i) the volume of fluid being greater than 80% of the collective volume and less than 100% of the collective volume, and (c)(ii) the peristaltic pump reciprocally moving fluid back and forth within the first and second lengths of tubing.

Example 13 includes the system of claim 1 wherein the number of rollers is one roller.

Example 14 includes the system of claim 1 wherein: the peristaltic pump has a number of predetermined positions for rollers; the number of rollers is less than the number of predetermined positions for rollers.

Example 15 includes the system of claim 2 wherein the peristaltic pump comprises at least one machine readable medium comprising a plurality of instructions that in response to being executed on a computing device, cause the peristaltic pump to generate between 30 and 80 pulses per minute within the first length of tubing.

Example 16 includes a system comprising: an artery, a vein, and a nerve; a first length of tubing adjacent at least one of the vein, the artery, and the nerve; a second length of tubing configured to couple to the first length of tubing; and a pump comprising a number of actuators; wherein when the system is an operative orientation the system is configured such that (b)(i) the second length of tubing couples to at least one of the number of actuators, (b)(ii) a first end of the first length of tubing is closed, (b)(iii) a first end of the second length of tubing is closed, (b)(iv) a second end of the first length of tubing is operatively coupled to a second end of the second length of tubing, (b)(v) the pump pulsates fluid within the first length of tubing in response to the number of actuators intermittently contacting the second length of tubing.

Thus, some embodiments include actuators, which may include rollers, plungers, shoes, wipers, lobes, and the like. Embodiments are not limited to any one type of pump.

Example 17 includes the system of claim 16 wherein: the number of actuators is no more than two actuators; the first length of tubing has a first flexibility; the second length of tubing has a second flexibility; the first flexibility is more flexible than the second flexibility.

The differences in flexibility ensure the majority of the pressure from the pump translates into pulsatility along a length of tubing adjacent the blood vessel of interest. However, some embodiments may use a single length of tubing to be adjacent the blood vessel of interest and to cooperate with an actuator of a pump. Also, as used herein a tube, such as tube 206, may include various lengths of tubes and does not necessarily entail a single monolithic (formed from a single piece) length of tube.

Example 18 includes the system of claim 17 wherein the first flexibility is configured to allow the first length of tubing to pulsate radially along a short axis of the first length of tubing in response to the pump pulsating fluid within the first length of tubing.

Such a short axis would be orthogonal to a long axis, such as axis 223.

Example 19 includes the system of claim 17 wherein: the first and second lengths of tubing collectively comprise a collective volume configured to retain the fluid; when the first and second lengths of tubing include a volume of fluid that is greater than 80% of the collective volume and less than 100% of the collective volume.

In an embodiment the first and second lengths of tubing may be shipped to customers already implanted within or adjacent a NVB and may already include the desired level of fluid that, when pumped by the pump (which is also sent to the client), results in a desired level of pulsatility (movement of the walls of the tube) that can be visualized using US (or some other form of imaging).

Example 20 includes a method comprising: coupling a second length of tubing to a first length of tubing, wherein (a)(i) the first length of tubing is adjacent a neurovascular bundle (NVB), (a)(ii) a first end of the first length of tubing is closed and a first end of the second length of tubing is closed, and (a)(iii) the first length of tubing has a first flexibility, the second length of tubing has a second flexibility, and the first flexibility is more flexible than the second flexibility; coupling the second length of tubing to a peristaltic pump, the peristaltic pump comprising a number of rollers that are less than four rollers; operating the peristaltic pump to radially pulsate the first length of tubing in response to the number of rollers intermittently contacting the second length of tubing.

As used herein, a tube "adjacent" a NVB may be a tube included within the NVB.

Example 21 includes the method of claim 20, wherein the first and second lengths of tubing collectively comprise a collective volume configured to retain the fluid; the method including collectively filling the first and second lengths of tubing to include a volume of fluid that is greater than 80% of the collective volume and less than 100% of the collective volume.

Example 22 includes a method comprising: locating a first length of tubing adjacent a neurovascular bundle (NVB), wherein (a)(i) a first end of the first length of tubing is closed, and (a)(ii) the first length of tubing has a first flexibility; providing a second length of tubing, wherein the (b)(i) the second length of tubing is configured to couple to the first length of tubing, (b)(ii) a first end of the second length of tubing is closed, and (b)(iii) the second length of tubing has a second flexibility that is less flexible than the first flexibility; providing a peristaltic pump, wherein (c)(i) the peristaltic pump has a number of predetermined positions for rollers; (c)(ii) the peristaltic pump includes a number of rollers that is less than the number of predetermined positions for rollers; containing the first length of tubing and the NVB in a first container; containing the peristaltic pump in a second container; communicating the first and second containers to a remotely located user.

Example 23 includes the method of example 22, wherein the first and second lengths of tubing collectively comprise a collective volume configured to retain the fluid; the method including: communicatively coupling the first and second lengths of tubing to each other; collectively filling the first and second lengths of tubing to include a volume of fluid that is greater than 80% of the collective volume and less than 100% of the collective volume.

In other embodiments the range (see 80-100 range in the paragraph immediately above) is between 95-99, 90-99, 85-99, 75-99, 70-99%.

Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A system comprising:
a neurovascular bundle (NVB) comprising an artery, a vein, and a nerve, wherein (a)(i) the artery directly contacts at least one of the vein and the nerve, (a)(ii) the vein directly contacts at least one of the artery and the nerve, and (a)(iii) the nerve directly contacts at least one of the vein and the artery;
a first length of tubing directly contacting at least one of the vein, the artery, and the nerve;
a second length of tubing to couple to the first length of tubing; and
a peristaltic pump comprising a number of rollers and the number of rollers is no more than three rollers;
wherein in an operative orientation (b)(i) the second length of tubing directly contacts at least one of the number of rollers, (b)(ii) a first end of the first length of tubing is closed and a second end of the first length of tubing is open, (b)(iii) a first end of the second length of tubing is closed and a second end of the second length of tubing is open, (b)(iv) the second end of the first length of tubing is communicatively coupled to the second end of the second length of tubing, (b)(v) the peristaltic pump reciprocally moves fluid back and forth within the first and second lengths of tubing in response to the number of rollers intermittently contacting the second length of tubing.

2. The system of claim 1 wherein the number of rollers is no more than two rollers.

3. The system of claim 1 wherein the first length of tubing is included in one of the artery or the vein.

4. The system of claim 1 wherein:
the first length of tubing has a first flexibility;
the second length of tubing has a second flexibility;
the first flexibility is more flexible than the second flexibility.

5. The system of claim 4 wherein:
the first length of tubing includes a first long axis that extends, when the first length of tubing is straight, from the first end of the first length of tubing to the second end of the first length of tubing;
the second length of tubing includes a second long axis that extends, when the second length of tubing is straight, from the first end of the second length of tubing to the second end of the second length of tubing;
the first flexibility is configured so the first length of tubing will pulsate in a direction orthogonal to the first long axis in response to the peristaltic pump reciprocally moving the fluid back and forth within the first and second lengths of tubing at a rate.

6. The system of claim 5 wherein the second flexibility is configured so the second length of tubing will not pulsate in a direction orthogonal to the second long axis in response to the peristaltic pump reciprocally moving the fluid back and forth within the first and second lengths of tubing at the rate.

7. The system of claim 1 wherein:
the first and second lengths of tubing collectively include a volume of fluid;
a first portion of the volume of fluid is included in the first length of tubing;
a second portion of the volume of fluid is included in the second length of tubing;
the peristaltic pump, the first length of tubing, the second length of tubing, and the volume of fluid are configured to lose prime when the peristaltic pump pumps at a rate.

8. The system of claim 1 wherein:
the first and second lengths of tubing collectively comprise a collective volume configured to retain a volume of the fluid;
the volume of the fluid is greater than 80% of the collective volume and less than 100% of the collective volume.

9. A system comprising:
an artery, a vein, and a nerve;
a first length of tubing adjacent at least one of the vein, the artery, or the nerve;
a second length of tubing configured to couple to the first length of tubing; and
a pump comprising at least one actuator;
wherein when the system is in an operative orientation the system is configured such that (a) the second length of tubing couples to the at least one actuator, (b) a first end of the first length of tubing is closed, (c) a first end of the second length of tubing is closed, (d) a second end of the first length of tubing is operatively coupled to a second end of the second length of tubing, (e) the pump pulsates fluid within the first length of tubing in response to the at least one actuator intermittently pumping the fluid.

10. The system of claim 9 wherein the first length of tubing is included in one of the artery or the vein.

11. The system of claim 9 wherein:
the first length of tubing has a first flexibility;
the second length of tubing has a second flexibility;
the first flexibility is more flexible than the second flexibility.

12. The system of claim 11 wherein:
the first length of tubing includes a first long axis that extends, when the first length of tubing is straight, from the first end of the first length of tubing to the second end of the first length of tubing;
the second length of tubing includes a second long axis that extends, when the second length of tubing is straight, from the first end of the second length of tubing to the second end of the second length of tubing;
the first flexibility is configured so the first length of tubing will pulsate in a direction orthogonal to the first long axis in response to the pump reciprocally moving fluid back and forth within the first and second lengths of tubing at a rate.

13. The system of claim 12 wherein the second flexibility is configured so the second length of tubing will not pulsate in a direction orthogonal to the second long axis in response to the pump reciprocally moving the fluid back and forth within the first and second lengths of tubing at the rate.

14. The system of claim 12 wherein the artery, vein, and nerve are included in a neurovascular bundle (NVB) and the NVB is one of an axillary NVB, a femoral NVB, a popliteal NVB, or a brachial NVB.

15. The system of claim 11 wherein:
the first and second lengths of tubing collectively include a volume of fluid;
a first portion of the volume of fluid is included in the first length of tubing;
a second portion of the volume of fluid is included in the second length of tubing;
the pump, the first length of tubing, the second length of tubing, and the volume of fluid are configured to lose prime when the pump pumps at a rate.

16. The system of claim 15 wherein:
at least one of the first and second lengths of tubing includes a visual marker that indicates when the first and second lengths of tubing collectively include the volume of fluid;
the visual marker is not located at the first end of the first length of tubing;
the visual marker is not located at the first end of the second length of tubing;
the visual marker is located between the first end of the first length of tubing and the first end of the second length of tubing.

17. The system of claim 15 wherein:
the first and second lengths of tubing collectively comprise a collective volume configured to retain the fluid;
the volume of fluid is greater than 80% of the collective volume and less than 100% of the collective volume.

18. The system of claim 11 wherein:
at least one of the first and second lengths of tubing includes a visual marker that indicates when the first and second lengths of tubing collectively include a volume of fluid;
the first and second lengths of tubing collectively comprise a collective volume configured to retain the volume of fluid;
the volume of fluid is greater than 80% of the collective volume and less than 100% of the collective volume;
a first portion of the volume of fluid is to be included in the first length of tubing;
a second portion of the volume of fluid is to be included in the second length of tubing;
the pump, the first length of tubing, the second length of tubing, and the volume of fluid are configured to lose prime when the pump pumps at a rate.

19. The system of claim 18 wherein:
the first length of tubing includes a long axis that extends, when the first length of tubing is straight, from the first end of the first length of tubing to the second end of the first length of tubing;
the first length of tubing is configured to collapse and expand, in a direction orthogonal to the long axis, in response to both (a) the volume of fluid being greater than 80% of the collective volume and less than 100% of the collective volume, and (b) the pump moving fluid back and forth within the first and second lengths of tubing;
the pump is a peristaltic pump.

20. The system of claim 9 wherein the pump comprises at least one machine readable medium comprising a plurality of instructions that in response to being executed on a computing device, cause the pump to generate between 30 and 80 pulses per minute within the first length of tubing.

* * * * *